United States Patent [19]

Parins

[11] Patent Number: 5,290,286

[45] Date of Patent: * Mar. 1, 1994

[54] BIPOLAR INSTRUMENT UTILIZING ONE STATIONARY ELECTRODE AND ONE MOVABLE ELECTRODE

[75] Inventor: David J. Parins, Columbia Heights, Minn.

[73] Assignee: Everest Medical Corporation, Minneapolis, Minn.

[*] Notice: The portion of the term of this patent subsequent to Mar. 30, 2010 has been disclaimed.

[21] Appl. No.: 987,924

[22] Filed: Dec. 9, 1992

Related U.S. Application Data

[62] Division of Ser. No. 790,490, Nov. 12, 1991, Pat. No. 5,197,964.

[51] Int. Cl.$^5$ ............................................. A61B 17/39
[52] U.S. Cl. ............................................................ 606/50
[58] Field of Search ................... 128/784, 786; 606/32, 606/37, 39–41, 45–50

[56] References Cited

U.S. PATENT DOCUMENTS

| | | |
|---|---|---|
| 373,399 | 11/1887 | Hamilton . |
| 1,798,902 | 3/1931 | Raney . |
| 1,881,250 | 6/1929 | Tomlinson . |
| 1,978,495 | 10/1934 | Landau . |
| 3,920,021 | 11/1975 | Hiltebrandt . |
| 4,060,087 | 11/1977 | Hiltebrandt et al. ................. 606/46 |
| 4,198,957 | 4/1980 | Cage et al. ........................... 606/37 |
| 4,353,371 | 10/1982 | Cosman . |
| 4,418,692 | 12/1983 | Guay . |
| 4,911,159 | 11/1990 | Johnson et al. ..................... 606/37 |
| 5,085,659 | 2/1992 | Rydell ................................. 606/47 |
| 5,197,964 | 3/1993 | Parins ................................. 606/48 |

*Primary Examiner*—Lee S. Cohen
*Assistant Examiner*—Marianne Parker
*Attorney, Agent, or Firm*—Haugen and Nikolai

[57] ABSTRACT

An electrosurgical instrument for the removal of tissue polyps and the like is disclosed. It features a bipolar pair of conductive electrodes for the cutting of tissue in which at least one electrode is moveable in relation to the other. These electrodes are mounted relative to an insulating plug, which is secured at the distal end of a tubular member. Pressure exerted on a thumb loop shifts the position of one electrode relative to the other. Upon application of RF voltage, the distance at which the electrodes are placed controls the amount of arcing which will occur between electrodes, when placed within a proper range. The electrodes are supplied with power from a standard RF energy source, controlled from a foot or hand switch. The insulating plug may further include metal traces disposed on the peripheral surface. When energized, these traces function as a bipolar pair of electrodes for effecting electrocoagulation of tissue and blood.

4 Claims, 3 Drawing Sheets

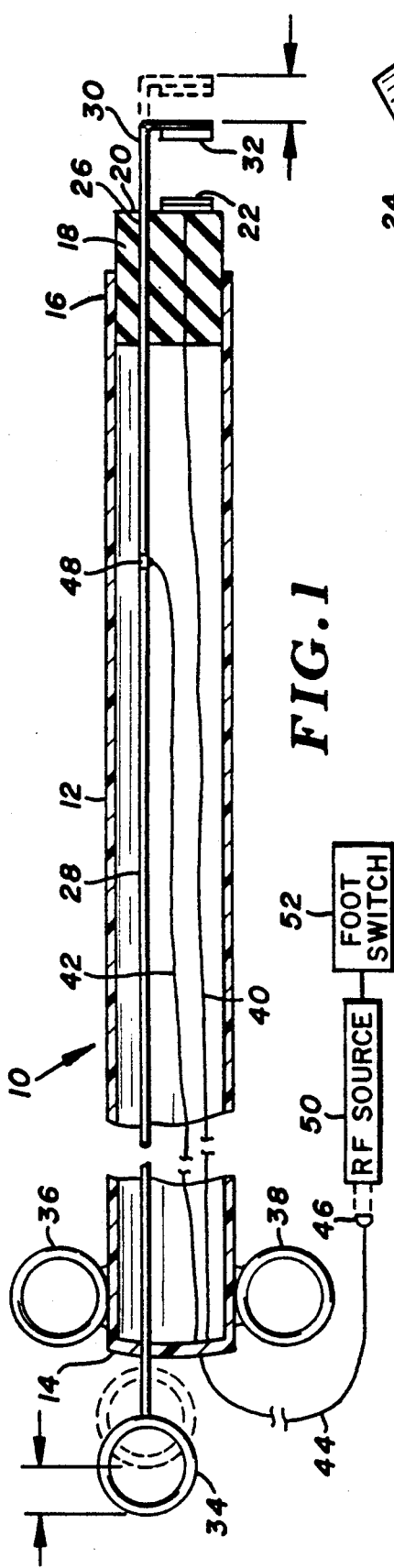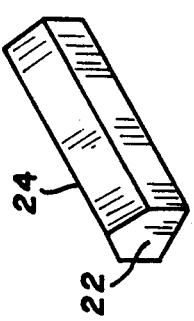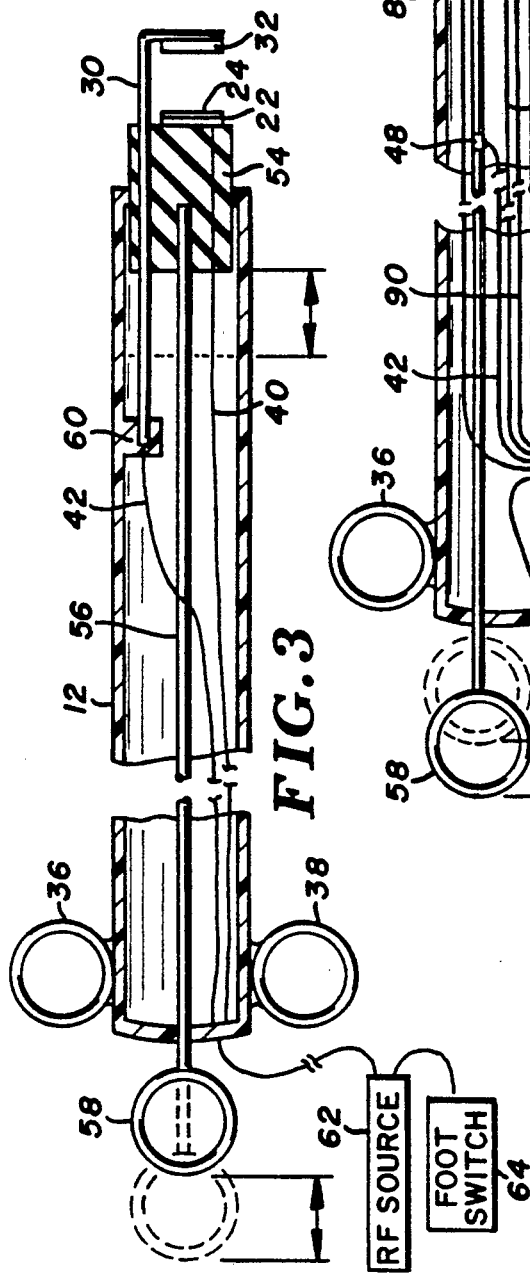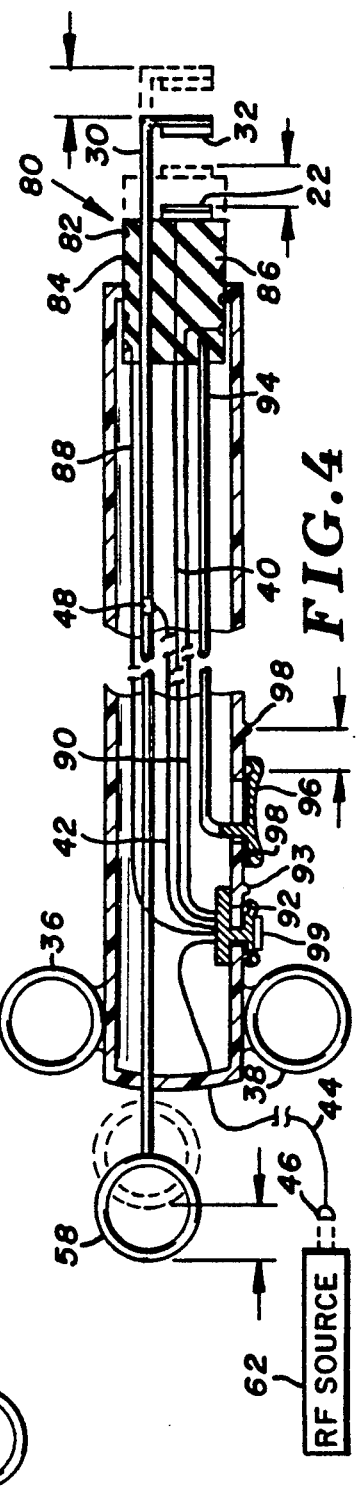

BIPOLAR INSTRUMENT UTILIZING ONE STATIONARY ELECTRODE AND ONE MOVABLE ELECTRODE

This is a Divisional of copending application Ser. No. 07/790,490, filed on Nov. 12, 1991 now U.S. Pat. No. 5,197,964.

BACKGROUND OF THE INVENTION

I. Field of the Invention

This invention relates generally to the design of an electrosurgical instrument and more particularly to an electrosurgical instrument for insertion into a laparoscopic trocar or endoscope and having one electrode which is movable relative to a stationary electrode. When the movable electrode is brought within a close predetermined distance to the fixed electrode and a voltage is applied across these electrodes, an arc is created for effecting radio frequency cutting or coagulation of a polyp or other tissue captured between the two electrodes. The device is especially adapted for trimming small polyps from the wall of the colon and, subsequently, cauterizing the remaining tissue at the site of the polyp removal. The device can also be utilized to coagulate vascular tissue areas.

II. Discussion of the Prior Art

Bipolar electrosurgical instruments typically feature a handle or housing which supports a pair of closely spaced conductive electrodes at a distal tip. These electrodes typically are stationary and extend distally from the tip and have a dielectric, such as air, therebetween. Neither is movable with respect to the other. In those electrosurgical instruments where at least one electrode is moveable, forceps-type electrodes which are movable by squeezing the electrodes toward one another, are commonly involved. In this forceps configuration, each electrode moves essentially equidistantly towards the other in one action.

U.S. Pat. No. 4,353,371, issued to Cosman, discloses a bipolar surgical instrument with longitudinally side-biting electrodes, which Is typical of the forceps-type designs. The forceps' blades are squeezed equidistantly towards one another along a longitudinal axis, as a coagulating potential is applied. Both blades of the forceps pivot towards one another within an insulating element which maintains electrical isolation at their bases. This configuration requires that the blades be placed at a right angle to the tissue to be cut if a smooth, even removal of tissue is desired.

U.S. Pat. No. 1,978,495, issued to Landau, discloses a medical instrument for the removal of tonsils. Pressure applied on a handle pushes an electrode toward a conductor. Increasing pressure eventually positions the electrode at a point where current is permitted to flow, whereupon a blade is advanced to sever the tonsil. In operation, a contact on a spring touches the conductor portion of the handle and maintains an open circuit for cutting. However, continuing pressure on the handle eventually advances the conductor forward until it is advanced to a region on the handle which is specifically dimensioned to break contact. Release of pressure on the handle permits the electrode to retreat and re-establish the circuit while the contact and handle are touching. Although exemplary of a movable electrode configuration, this device is awkward in applications other than tonsillectomies.

U.S. Pat. No. 373,399, issued to Hamilton, discloses an electrode for forming clots in varicose veins. In this device, a J-shaped rod has an electrode placed at its tip. A second electrode is placed in opposing relation on a slightly curved rod. Each electrode terminates at a conducting wire and is held within a pair of retainers. The "J"-shaped rod is held securely, but the curved rod may be displaced Proximally or distally. An adjustable stop regulates the extent of proximal or distal movement and, thus, prevents the approach of the two electrodes beyond a desired limit. After the device is positioned within body tissues, a coagulating electrical current is applied. Although this device also provides an example of a configuration for a movable electrode, this "J"-shaped rod requires greater clearance than is available in some electrosurgical applications.

It is accordingly a principal object of the present invention to provide a new and improved method and apparatus for bipolar cauterization of tissue featuring one stationary electrode and one movable electrode.

Another object of the present invention is to provide a new and improved method and electrocauterizing apparatus for encompassing polyps and the like then severing them in a guillotine fashion.

It is yet another object of the present invention to provide such a new and improved electrocauterizing apparatus dimensioned for insertion within a laparoscopic trocar or endoscope.

A further object of the present invention is to provide an electrocauterizing apparatus with a moveable electrode, further including electrocoagulating traces for coagulation of blood in the treatment region.

SUMMARY OF THE INVENTION

An electrosurgical instrument for trimming small polyps from the wall of the colon and, subsequently, cauterizing the tissue at the site of the polyp material is disclosed. Five embodiments are shown, each of which includes one stationary electrode and one movable electrode. When the movable electrode is brought into a close, predetermined distance from a fixed electrode and a voltage is applied across the electrodes, an arc is created for effecting electrosurgical cutting of a polyp or coagulating other tissue which has been captured between the two electrodes. The electrodes have a rectangular shape and operate in a guillotine fashion. In one embodiment, the outer electrode moves with respect to the remainder of the assembly. In another embodiment, an inner electrode moves with respect to a fixed outer electrode. In yet another embodiment, a hook-type blade contains the electrode and either an outer hook or an inner, reciprocating blade electrode, or both, may be moveable.

The electrodes are fitted into a distal insulating plug, which is inserted into the distal end of the instrument. An optional electrocoagulating feature includes metal traces inlaid upon the peripheral surface of the insulating plug. These traces act as a bipolar pair when RF voltage is applied across them, thus electrocoagulating tissue and fluids with which they are brought in contact.

The aforementioned objects and advantages of the invention will become subsequently apparent and reside in the details of construction and operation as more fully hereinafter described and claimed, reference being had to the accompanying drawings forming a part thereof, wherein like numerals refer to like parts throughout.

DESCRIPTION OF THE DRAWINGS

FIG. 1 depicts a partial,, side cross-sectional view of a preferred embodiment of the present invention;

FIG. 2 depicts a perspective, enlarged view of a preferred electrode configuration used on the device of FIG. 1;

FIG. 3 depicts a partial, side cross-sectional view of an alternative embodiment of the present invention;

FIG. 4 depicts a partial, side cross-sectional view of another alternative embodiment of the present invention;

DESCRIPTION OF THE PREFERRED EMBODIMENT

Figure 5:
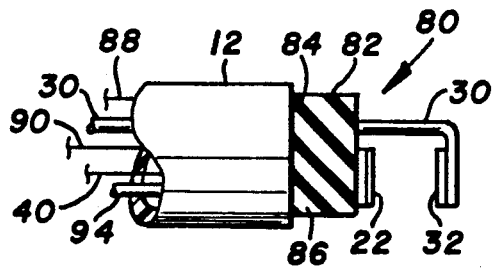
FIG. 5 is a perspective view of the distal end of the embodiment of FIG. 4.

A preferred embodiment of the bipolar electrosurgical instrument of the present invention is shown in FIG. 1. Generally designated as 10, the instrument is comprised of a tubular member 12 having a proximal end 14 and a distal end 16. Fitted into the distal end 16 is a cylindrical insulating plug 18, preferably comprised of ceramic, or the like. Mounted upon a distal end surface 20 of plug 18 is a surface electrode 22, preferably of stainless steel, tungsten or tungsten alloy. With no limitation intended, and as better seen in FIG. 2, electrode 22 preferably has a pentagon shaped cross-section, providing a knife edge 24 facing outward from the end 20 of insulating plug 18. Distal end surface 20 of plug 18 may preferably be generally circular or oval.

A longitudinal bore 26 is drilled or otherwise formed lengthwise through plug 18, communicating with the lumen of tubular member 12. An actuator or push rod member 28 is preferably made of plastic or covered with a nonconductive material and extends through tubular member 12. Near the distal end of tubular member 12, it is joined, as at junction 48, with an "L"-shaped rigid support member or rod, such as stainless steel rod 30, which is inserted through bore 26. Rod 30 further includes blade electrode 32, preferably of stainless steel, tungsten or tungsten alloy, and which is disposed to operably cooperate with surface electrode 22.

The actuator member 28 extends through the length of the tubular member 12 and terminates at its proximal end in a thumb loop 34. Alternatively, the rigid support rod 30 may be comprised of a one-piece rod which extends the full length of member 12 and protrudes from its proximal end, as depicted in FIG. 4. A pair of rigid finger loops 36 and 38 are attached at the proximal end 14 of the tubular member 12 to provide a secure grip for moving actuator member 28 and concomitantly, stainless steel support rod 30, reciprocally within the bore 26, causing electrode 32 to move toward or away from electrode 22 on plug 18.

A pair of flexible conductive wires 40 and 42 are insulated from one another and extend through tubular member 12. A conventional cord 44, with electrical connector 46 on its free end, is electrically joined to the wires 40 and 42 at their proximal ends to facilitate their connection to an electrosurgical generator. The distal ends of wires 40 and 42 are electrically joined to electrodes 22 and 32, respectively. Specifically, conductive wire 40 extends the full length of tubular member 12 from cord 44 to surface electrode 22. Conductive wire 42 extends from cord 44 to a junction point 48, where it is mechanically and electrically joined to steel rod 30. When the thumb loop 34 and actuator member 28 are formed from plastic, there is no danger of shock to the surgeon. If a one-piece metal push rod is used, the thumb loop 34 should be appropriately insulated.

It is suggested that cord 44 be supplied with RF voltage from an RF source 50. Control of this supply may be attained by use of a conventional on/off foot switch 52, as known in the art. When the foot switch is depressed, a circuit is completed and electrical current is permitted to flow from the electrosurgical generator 50 and through electrodes 22 and 32 when tissue is captured therebetween. One skilled in the art will readily recognize that a finger-operated switch, such as switch 92 in FIG. 4, mounted on housing 12 is equally useful to provide current in a controlled fashion to electrodes 22 and 32.

FIG. 3 depicts a cross-sectional view showing an alternative tip arrangement for the present invention. In this embodiment, blade electrode 32 is mounted on a rigid support member 30 which is stationary. However, the insulating plug 54 is made moveable by virtue of being rigidly affixed to an actuator member such as stainless steel rod 56. A thumb loop 58 is affixed at its proximal end and coated with a thin, insulative coating (not shown). Thumb loop 58 is positioned in opposable relation to finger loops 36 and 38 on the tubular member 12, as in the previous embodiment. Thus, moving thumb loop 58 in a distal direction will simultaneously extend plug 54 beyond the distal end of member 12 and toward stationary blade electrode 32. Stationary blade electrode 32 may be mounted on support rod 30, which is secured in retainer 60 comprised of a block of plastic. Movement of thumb loop 58 brings cutting edge 24 toward or away from stationary electrode 32. When radio frequency (RF) energy from source 62 is applied using foot switch 64, a polyp or other tissue segment held between electrodes 22 and 32 will be severed.

FIG. 4 depicts an alternative embodiment featuring a variation of the plug shown in FIG. 3 and eliminating the foot switch option. Designated generally as 80, this cylindrical plug can similarly be made to extend outward from the distal end of tubular member 12 by movement of a thumb switch. As better seen in FIG. 5, the plug 80 features metal traces 82 and 84 inlaid in noncontacting and spiral relation upon the peripheral surface 86. When energized, these traces 82 and 84 function as bipolar electrodes for effecting electrocoagulation of tissue and blood. Additional flexible wire conductors 88 and 90 pass through the tubular member and supply RF voltage to these traces, which are preferably comprised of a tungsten alloy. To activate the electrocoagulating electrodes 82 and 84, conductors 88 and 90 are joined to thumb switch 92. When thumb switch 92 is advanced distally to lock on detent 93, the circuit is completed and the traces 82 and 84 are energized. When the circuit is completed, RF voltage is supplied via cord 44 from RF source 62.

The electrodes 22 and 32 must be energized independently from traces 82 and 84. Push button 99 mounted on thumb switch 92 is connected to conductors 40 and 42 and cord 44. It permits the user to exactly control the duration of cutting by the duration it is depressed.

The plug 80 may also be extended or retracted. A rigid actuator member 94 is affixed to a sliding thumb switch 96. Movement in a distal direction extends the plug 80, while proximal movement retracts it. Slippage is prevented by detents 98.

Figure 6:
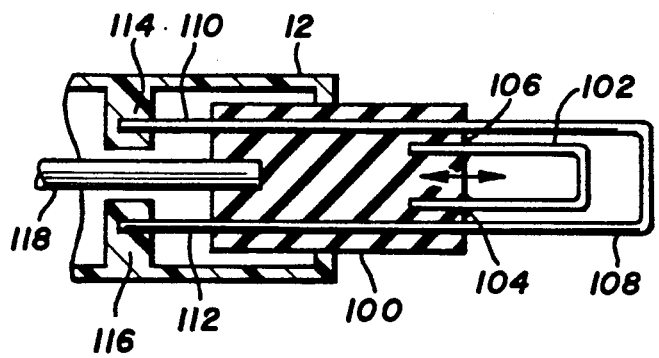
FIG. 6 depicts a side, cross-sectional view of an alternative tip arrangement for the present invention.
Figure 7:
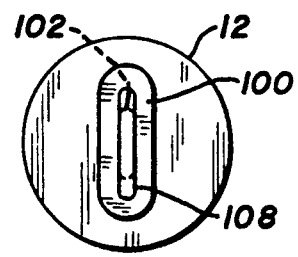
FIG. 7 depicts an end view of the tip arrangement of FIG. 6.
Figure 8:
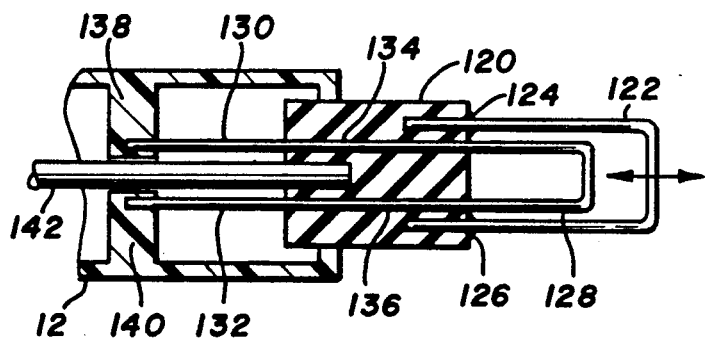
FIG. 8 depicts a side, cross-sectional view of yet another tip arrangement for the present invention.

FIGS. 6 and 8 depict alternative embodiments for the seductive electrodes 22 and 32 of FIGS. 1–4. A pair of generally U-shaped electrodes either pass through or are secured within a plug member, such as plug 100. In FIG. 6, the legs of the moveable U-shaped electrode 102 are embedded and fixed within an oval-shaped plug 100, better seen in FIG. 7. They are securely held in place with, for example, beads of potting material 104 and 106. Stationary electrode 108 is dimensioned to be slightly larger in total surface area than electrode 102. Bores have been drilled through the insulating plug 100 to receive legs 110 and 112 of electrode 108. These legs 110, 112 extend into tubular member 12 and are secured in a pair of nonconductive retainers 114 and 116. A rigid actuator means, as depicted in FIG. 3, includes a stainless steel rod 118, which extends through tubular member 12 to a thumb loop, as in previously described embodiments. The rod 118 is securely affixed at its distal end to plug 100 so translational movement of the thumb loop causes the end plug carrying electrode 102 to be displaced along the longitudinal axis of tubular member 12 toward or away from fixed electrode 108.

The converse is depicted by plug 120 in FIG. 8. The legs of moveable electrode 122 are embedded within plug 120 and secured with potting material 124 and 126. Fixed electrode 128 is disposed coaxially with moveable electrode 122 and has legs 130 and 132 which extend through bores 134 and 136 in plug 120 to retainers 138 and 140 inside tubular member 12. Plug 120 is similarly affixed to an actuator means, here depicted as stainless steel rod 142, which extends to a thumb loop (not shown), as in previous embodiments.

Figure 9:
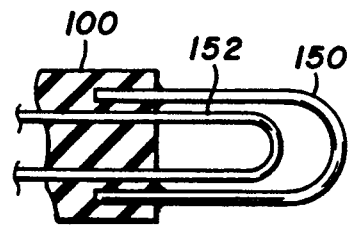
FIG. 9 depicts a side, cross-sectional view of another alternative tip arrangement for the present invention.
Figure 10:
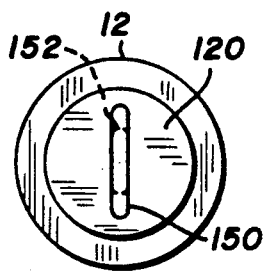
FIG. 10 depicts an end view of the tip arrangement of FIG. 9.

It is well within the contemplation of one skilled in the art that although the electrodes in FIGS. 6 and 8 are depicted as being somewhat rectangular in shape, electrodes 102, 108, 122 and 128 may be dimensioned in various curved configurations as well. An example is provided in FIG. 9, wherein electrodes 150 and 152 feature distal curves to provide a scoop-like excision in tissue. Furthermore, as better seen in FIG. 10, plug 120 may have a circular distal surface.

Figure 12:
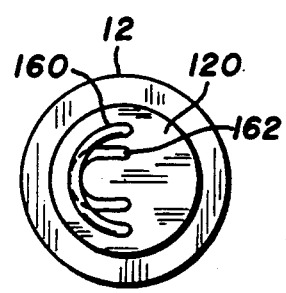
FIG. 12 depicts an end view of the tip arrangement of FIG. 11.
Figure 11:
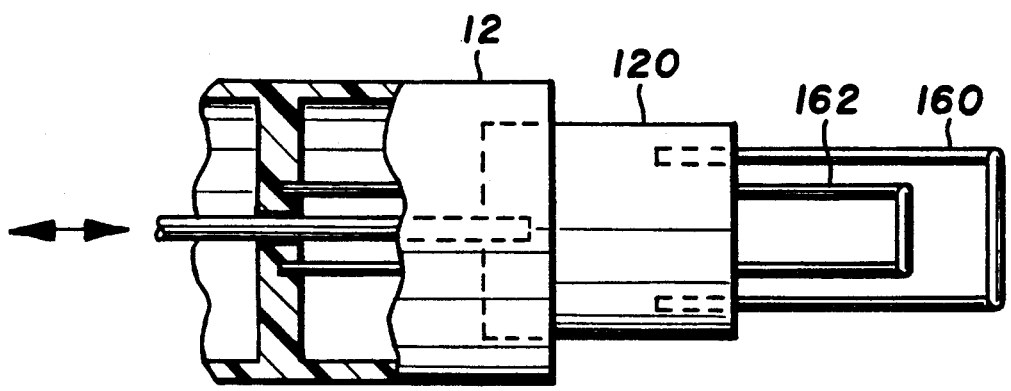
FIG. 11 depicts a side, cross-sectional end view of yet another electrode configuration for the present invention.

One skilled in the art will appreciate that many variations in electrode configuration are possible, but such variations do not depart from the spirit of the present invention. For example, FIGS. 11 and 12 show a variant of the embodiment of FIG. 10, in which the electrode tips 160 and 162 have been flattened into a plane perpendicular to that of the longitudinal axis of the tubular member 12.

In operation, a surgeon grasps tubular member 12 at its proximal end, inserting his thumb and fingers in loops 34, 36 and 38. The distal portion of the electrosurgical instrument is then advanced through a laparoscopic trocar or endoscope and the distal end carrying or otherwise supporting the bipolar electrodes is positioned near the tissue to be removed. By moving thumb loop 34 toward tubular member 12, electrode 30 in FIG. 1 is moved distally from electrode 22. In the embodiment of FIG. 8, electrode 122 is moved distally from electrode 128. In the embodiments of FIGS. 3, 4 and 5, the thumb loop 34, 54 is pulled proximally. This draws the plug (54, 86 or 100) proximally and away from the electrode (32 or 108). In all embodiments, movement of the thumb loop, as herein described, provides a gap into which the tissue to be excised is inserted. Upon reciprocal movement and simultaneous application of radio frequency energy, the tissue is electrocauterized and severed. To provide enhanced electrocoagulation, traces such as depicted in FIG. 4, may be included on all embodiments.

This invention has been described herein in considerable detail in order to comply with the Patent Statutes and to provide those skilled in the art with the information needed to apply the novel principles and to construct and use such specialized components as are required. However, it is to be understood that the invention can be carried out by specifically different equipment and devices and that various modifications, both as to equipment details and operating procedures, can be accomplished without departing from the scope of the invention itself.

What is claimed is:

1. An electrosurgical instrument for the removal of tissue polyps and for steming the flow of blood following such removal, comprising:
   (a) a tubular member having a distal end, a proximal end, and a lumen extending therebetween, and having a longitudinal axis extending between said distal and proximal ends;
   (b) an insulating plug affixed to said tubular member at said distal end and having a distal surface generally perpendicular to said longitudinal axis;
   (c) a rigid support member extending from said distal surface of said insulating plug, and projecting parallel to said longitudinal axis and having a distal end;
   (d) a first electrode mounted on said distal surface of said insulating plug;
   (e) a second, generally U-shaped metal wire electrode extending from said distal end of said rigid support member dimensioned to lie proximal of said first electrode, with said first electrode disposed coaxially with said second electrode, and positioned to enable electrical coaction with said first electrode;
   (f) a pair of flexible conductive wires extending through said lumen of said tubular member and conductively joined, individually, to said first and second electrodes for allowing electrical energizing of said electrode;
   (g) an actuator means for affecting translational movement of one of said first and second electrodes in a direction parallel to said longitudinal axis, for bringing said first and second electrode within a predetermined distance of one another; and
   (h) a hand switch in electrical communication with one of said first and second electrodes.

2. An electrosurgical instrument as in claim 1, further including a pair of metal traces disposed upon said insulating plug for effecting electrocoagulation of tissue.

3. An electrosurgical instrument as in claim 1, wherein said plug is cylindrical.

4. An electrosurgical instrument as in claim 1, wherein said plug is an oval-ended cylinder.

* * * * *